United States Patent [19]

Amisar

[11] Patent Number: 5,753,513
[45] Date of Patent: May 19, 1998

[54] REAGENT FOR THE IDENTIFICATION OF COCAINE

[75] Inventor: Shai Amisar, Jerusalem, Israel

[73] Assignee: Erez Forensic Technology Ltd., Israel

[21] Appl. No.: 786,113

[22] Filed: Jan. 17, 1997

[30] Foreign Application Priority Data

Jan. 22, 1996 [IL] Israel ........................................ 116850

[51] Int. Cl.$^6$ .......................... G01N 33/00; G01N 21/78; G01N 31/22; C07D 451/02
[52] U.S. Cl. ................................ 436/96; 436/901; 546/124
[58] Field of Search ...................... 436/96, 901; 546/124

[56] References Cited

U.S. PATENT DOCUMENTS

| | | | |
|---|---|---|---|
| 4,104,027 | 8/1978 | Carroll | 436/92 |
| 4,812,413 | 3/1989 | Glattstein | 436/92 |
| 5,457,054 | 10/1995 | Geisinger et al. | 436/92 |

*Primary Examiner*—Alan L. Rotman
*Attorney, Agent, or Firm*—Londa and Traub LLP

[57] ABSTRACT

The invention provides a reagent for the presumptive identification of cocaine, cocaine salts and phencyclidene comprising cobalt thiocyanate, at least one poly-hydroxy alcohol and a third component selected from the group consisting of a polyether, a silicon derivative of a polyether and mixtures thereof, with the proviso that the poly-hydroxy alcohol is not glycerol.

8 Claims, No Drawings

REAGENT FOR THE IDENTIFICATION OF COCAINE

The present invention relates to a reagent for the presumptive identification of cocaine, cocaine salts and phencyclidene.

As will be realized, on numerous occasions a police officer has to determine whether or not a suspected material contains a prohibited drug and thus quickly establish probable cause.

Often the laboratory is closed, or many miles away, and he has no way of making this determination. A test kit can help an officer detect the presence of such drugs of abuse.

The quickest test known for drug identification is a color test in which the response of the drugs to a specific reagent makes it possible to assign the drug to one or more classes.

In order to obtain sufficient evidence to detain a suspected drug peddler or drug user, chemical spot test kits have been commercially developed and are used by many law enforcement agencies for the identification of narcotics and drugs of abuse.

Most of the commercial test kits for the presumptive identification of cocaine are based on contacting cocaine and its salts with cobalt thiocyanate solutions which results in the formation of a relatively water insoluble turquoise complex.

The relative simplicity of the cobalt thiocyanate test made its use feasible outside the laboratory and created a demand for a variation with increased specificity.

The standard Scott Test (L. J. Scott, Specific Field Test for Cocaine, Microgram, VI, 179(1973), is based on the use of cobalt thiocycanate as incorporated in a commercial test kit which contains the chemicals required to perform the test in a prefilled, hermetically sealed glass ampules.

There are three glass ampules:

(1) Cobalt thiocycanate reagent in a 1:1 water glycerine solution;
(2) Concentrated hydrochloric acid; and
(3) chloroform.

The glass ampules are placed into a pouch. The pouch is folded at the top, and a clip is placed over the fold which seals the package.

The following is the recommended test procedure when using this kit:

(1) Remove the plastic clip from the test pack and open the pouch.
(2) Place the suspect cocaine into the pouch, tap or jar test package, making sure most of this falls to the bottom of the pack.
(3) Refold the pouch at the original fold point and replace the clip securely, sealing the package.
(4) The cobalt thiocyanate ampule should then be broken, releasing the reagent to mix with the suspect. This can be accomplished by squeezing the center with the thumb and forefinger. When breaking the ampule, the fingers are pushing against smooth glass walls. If the ampule is squeezed at the extreme top or bottom, It could conceivably break through the plastic pouch. Therefore apply even pressure at the center of the ampule. No attempt should be made to crush the small glass particles after the ampule is broken.
(5) With the suspected material in the test package and the reagent released, gently shake or agitate.
(6) If turquoise blue precipitate is formed the second and the third ampules should be broken.
(7) Before discarding the test pack, remove clip and add one measure of acid neutralizer.
(8) Reseal test packs with clips and discard in a tamper-free disposal unit.

This method has several disadvantages:

(1) Complicated procedure;
(2) It uses corrosive concentrated hydrochloric acid; and
(3) Trace amount of cocaine cannot be detected.

Furthermore, in U.S. Pat. No. 4,104,027 there is described a reagent comprising of two solutions—an aqueous solution of cobalt thiocyanate, and a solution of stannous chloride and HCI in water. Presumably these two solutions may distinguish between lidocaine and cocaine: Administering the suspected powder to the first reagent yields a blue color with cocaine, dibucaine, procaine or tetracaine. A deep pink color in which flecks of blue green color, indicating lidocaine, a deep pink color without blue flecks indicates antipyrine or phendimetrazine.

Adding the second solution yields a pink color within which are flecks of blue green color, indicating lidocaine or dibucaine.

It has been found that despite claims, the described reagents have the following disadvantages:

(a) When performing the above sequence on very small quantities of cocaine, there is no color change and the reagents remain pink; and
(b) When doing the same on a larger quantity of lidocaine, the color of the whole solution is blue, like the color described for cocaine, without any flecks, etc.

Despite these known disadvantages, in the last fifteen years no one has proposed or commercialized an improved test kit which would ameliorate these problems, with the exception of the test kit described and claimed in our U.S. Pat. No. 4,812,413 which is directed to an aerosol spray reagent for the presumptive identification of a prohibited drug such as cocaine, cocaine salts and phencyclidene which comprises cobalt thiocyanate, a polyol in which said drugs are selectively soluble, a halogenated alkane propellant, a non-ionic emulsifier different from said polyol and a silicon anti-foam agent.

Bearing the above in mind, there is now provided a reagent for the presumptive identification of cocaine, cocaine salts and phencyclidene comprising cobalt thiocyanate, at least one poly-hydroxy alcohol and a third component selected from the group consisting of a polyether, a silicon derivative of a polyether and mixtures thereof with the proviso that said poly-hydroxy alcohol is not glycerol.

This reagent is superior to former reagents because it does not give a positive reaction with lidocaine, which is the main source of mistaken identification of drugs in regular police field work.

Furthermore, this reagent does not destroy the examined sample which enables the user to detect cocaine by other methods in the reacted sample.

This reagent is further advantageous in the fact that it is sensitive to small amounts of cocaine which are too small to be identified in the formerly described methods where formation of flecks in a solution is sought.

This reagent is also advantageous in the fact that it is a "Yes/No" result based reagent, which is not susceptible to personal interpretation, as is the case in most former reagents.

This reagent is further advantageous in the fact that it is a simple, one solution reagent, which does not require handling of several solutions and mixtures in a multi-step process. A drop of the reagent is applied to the sample, the development of a light-blue-turquoise color indicates the presence of cocaine or its salts, phencyclidene. When applied to lidocaine, there is no color reaction.

Another major advantage is that this reagent does not comprise any hazardous component, such as concentrated hydrochloric acid or chloroform.

Because of the above-mentioned advantages, the reagent can be used as a pre-packaged spray reagent, which is the best method of dispensing.

Being a one, uniform single phase solution, the production procedure of this reagent is much simpler than former reagents, including the one described in our own U.S. Pat. No. 4,812,413 which uses two non-miscible solutions.

Cocaine free base may not react (in some cases) to the said reagent. It was found that adding an acid to the reagent results in an instant reaction to any form of cocaine, including the base, without destroying the cocaine sample and without interfering with the selectivity of the reagent.

Thus, in preferred embodiments of the present invention, said reagent further comprises an acid.

It is noted that using only one polyol, as is taught by the original Scott Reagent (Scott, L. J. Microgram, VI, 179 (1973)), where the polyol is glycerol, and in U.S. Pat. No. 4,812,413 will render the reagent non-specific in the sense that it reacts to lidocaine in the same color as cocaine. Furthermore, it was found that using glycerol (either instead or in addition to one of the specified multi-hydroxy-alcohols), makes the reagent non-specific and reactive to lidocaine.

Thus, the present invention provides an improved cobalt thiocyanate reagent, which is fast reacting, highly sensitive to even trace amounts of drug, and does not react to lidocaine, which is a major source of mistakes in the field.

In said reagent, said poly-hydroxy alcohol is preferably selected from the group consisting of propylene glycol, 1,3-propane-diol, 1,4-butane-diol, ethylene glycol, and mixtures thereof. Said polyether is preferably selected from the group consisting of poly-ethylene glycol (PEG) 200, PEG-400, PEG-600, diethylene glycol mono ethyl-ether, polypropylene glycol (PPG) 200, PPG-400, and PPG-600, and said acid is preferably selected from the group consisting of ortho-phosphoric acid, acetic acid, tri-fluoro acetic acid, hydrochloric acid and citric acid.

A preferred reagent according to the present invention comprises about 0.5 to 5% cobalt thiocyanate, 30 to 75% water, 20 to 60% poly-hydroxy alcohol, 2 to 10% polyether, and 0.1 to 2.5% acid.

While the invention will now be described in connection with certain preferred embodiments n the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

A reagent containing 1.5 gram cobalt thiocyanate, 5.2 gram 1,4-butane-diol, 34.7 gram 1,3-propane-diol, 55.4 gram water and 3.2 gram ortho-phosphoric acid was prepared.

EXAMPLE 2

A reagent containing 2.5 gram cobalt thiocyanate, 3 gram diethylene glycol mono methyl ether, 28 gram 1,3-propane-diol, and 66.5 gram water was prepared.

EXAMPLE 3

A reagent containing 0.86 gram cobalt thiocyanate, 4 gram PEG 400, 36.8 gram propylene glycol, 57.74 gram water, 0.6 gram tri fluoro acetic acid was prepared.

EXAMPLE 4

A reagent containing 1.15 gram cobalt thiocyanate, 5.4 gram PEG 400, 46 gram propylene glycol, 45.3 gram water, 2.15 gram ortho-phosphoric acid was prepared.

EXAMPLE 5

A reagent containing 1.7 gram cobalt thiocyanate, 7.2 gram PPG 400, 37 gram propylene glycol, 52.1 gram water, 2 gram acetic acid was prepared.

EXAMPLE 6

A reagent containing 1.1 gram cobalt thiocyanate, 3 gram PEG 200, 3.5 gram PEG 400, 29 gram propylene glycol, 61.4 gram water, 2 gram hydrochloric acid 32% was prepared.

COMPARATIVE EXAMPLE A

The reagents described in the prior art were tested with lidocaine and cocaine and the results were as follows:

A small amount of cocaine HCl (about 100 microgram) was placed in a plastic pouch containing a commercial Scott Reagent (cobalt thiocyanate solution, hydrochloric acid, chloroform—in sealed ampules). After breaking the ampules no color was obtained.

100 mg of Lidocaine HCl were placed in such a plastic bag, and the ampules were broken. An immediate blue color, similar to that obtained with cocaine, was observed.

10 micrograms of lidocaine HCl were placed on a filter paper, and sprayed with "Coca-Test" (a commercial product based on U.S. Pat. No. 4,812,413) An immediate turquoise color, similar to that obtained with cocaine, was observed.

10 micrograms lidocaine HCl were placed on a filter paper, and sprayed with the reagent as described in Example 4 above. No color was observed.

10 micrograms of cocaine HCl were placed on a filter paper, and sprayed with the reagent as described in Example 4 above. An immediate turquoise color was observed.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A reagent for the presumptive identification of cocaine, cocaine salts and phencyclidene comprising cobalt thiocyanate, at least one poly-hydroxy alcohol and a third component selected from the group consisting of a polyether, a silicon derivative of a polyether and mixtures thereof, with the proviso that said poly-hydroxy alcohol is not glycerol.

2. A reagent according to claim 1 comprising a mixture of at least two poly-hydroxyalcohols.

3. A reagent according to claim 1, wherein said poly-hydroxy alcohol is selected from the group consisting of propylene glycol, 1,3-propane-diol, 1,4butane-diol, ethylene glycol, and mixtures thereof.

4. A reagent according to claim 1 further comprising an acid.

5. A reagent according to claim 4, wherein said acid is selected from the group consisting of an acetic acid, a hydrochloric acid, a citric acid and a phosphoric acid.

6. A reagent according to claim 5, wherein said acid is selected from the group consisting of ortho-phosphoric acid, acetic acid, tri-fluoro acetic acid, hydrochloric acid and citric acid.

7. A reagent according to claim 1, wherein said polyether is selected from the group consisting of poly-ethylene glycol (PEG) 200, PEG-400, PEG-600, diethylene glycol mono ethyl-ether, poly-propylene glycol (PPG) 200, PPG-400, and PPG-600.

8. A reagent according to claim 1 comprising about 0.5 to 5% cobalt thiocyanate, 30 to 75% water, 20 to 60% of at least one poly-hydroxy alcohol, 2 to 10% of a polyether, and 0.1 to 2.5% of an acid.

* * * * *